(12) United States Patent
Ozturk et al.

(10) Patent No.: US 9,758,501 B2
(45) Date of Patent: Sep. 12, 2017

(54) FLUOROPHORE 3-HYDROXYFLAVONE

(71) Applicant: TUBITAK (TURKIYE BILIMSEL VE TEKNOLOJIK ARASTIRMA KURUMU), Ankara (TR)

(72) Inventors: Turan Ozturk, Istanbul (TR); Mehmet Saip Eroglu, Istanbul (TR); Asli Capan, Istanbul (TR); Muslum Akgoz, Kocaeli (TR)

(73) Assignee: TUBITAK (TURKIYE BILIMSEL VE TEKNOLOJIK ARASTIRMA KURUMU), Ankara (TR)

( * ) Notice: Subject to any disclaimer, the term of this patent is extended or adjusted under 35 U.S.C. 154(b) by 0 days.

(21) Appl. No.: 15/028,437

(22) PCT Filed: Oct. 10, 2013

(86) PCT No.: PCT/IB2013/059252
§ 371 (c)(1),
(2) Date: Apr. 11, 2016

(87) PCT Pub. No.: WO2015/052555
PCT Pub. Date: Apr. 16, 2015

(65) Prior Publication Data
US 2016/0251329 A1    Sep. 1, 2016

(51) Int. Cl.
*C07D 311/30* (2006.01)
(52) U.S. Cl.
CPC .................................. *C07D 311/30* (2013.01)
(58) Field of Classification Search
CPC .................................................... C07D 311/30
See application file for complete search history.

(56) References Cited

FOREIGN PATENT DOCUMENTS

WO    WO2007057782 A2    5/2007

OTHER PUBLICATIONS

Turan Ozturk et al"New 3-hydroxyflavone derivatives for probing hydrophobic sites in microhetergeneous systems", Tetrahedron, Elsevier Sciene Publishers,Amsterdam,NL, vol. 63 No. 41, Aug. 31, 2007, pp. 10290-10299.
V.V.Moroz et al"The properties of 4'-n,n-dimethylaminoflavonol in the ground and excited states", Russian Journal of Physical Chemistry, vol. 82, No. 9, 2008,pp. 1464-1469.
Gora M'Maye et al"Fluorescent dyes undergoing intramolecular proton transfer with improved sensitivity to surface charge in lipid bilayers", Photochem. Photobiol. Sci., vol. 6, Nov. 23, 2006, pp. 71-76.
Alexander P.Demchenko et al"Excited-state proton coupled charge transfer modulated by molecular structure and media polarization", Chem.Soc.Rev., vol. 2013, No. 42, Dec. 20, 2012, pp. 1379-1408.
Simay Gunduz et al"Facile synthese of 3-hydroxyflavones", Organic Letters, vol. 14, No. 6, Mar. 8, 2012, pp. 1576-1579.
P. Chou et al"The Proton-transfer laser, gain spectrum and amplification of spontaneous emission of 3-hydroxyflavone" Phys. Chem. 1984, No. 88,pp. 4596-4599.
Alexander Sytnik et al"Interplay between excited-state intramolecular proton gransfer and charge transfer in flavonols and their use as proten-binding-site fluorescence probes", Proc. Natl. Aca. Sci. USA, vol. 91, Dec. 1994,pp. 11968-11972.
Munna Sarkar et al"Effect of reverse micelles on the intramolecular excited state proton transfer and dual luminescence behaviour of 3-hydroxyflavone", Spectrochimica Acta Part A,1996, No. 52, pp. 275-278.
Jayesh R Dharia et al"Synthesis and characterization of wavelength-shifting monomers and polymers based on 3-hydroxyflavone", Macromolecules 1994, No. 27, pp. 5167-5172.
Dale McMorrow et al"Intramolecular excited-state proton transfer in 3-hydroflavone hydrogen-bonding solvent perturbations", Phys. chem. 1984, No. 88, pp. 2235-2243.

*Primary Examiner* — Matt Mauro
(74) *Attorney, Agent, or Firm* — Gokalp Bayramoglu

(57) ABSTRACT

The present invention discloses the syntheses of new 3-hydroxyflavone salts with defined structures, which are suitable for sensor applications for sensing anions, cations, DNA chains and organic compounds soluble in highly polar solvent like water.

1 Claim, 4 Drawing Sheets

FLUOROPHORE 3-HYDROXYFLAVONE

FIELD OF INVENTION

The present invention relates to 3-hydroxyflavone having specified structure, which are expected to be applied as sensors for sensing anions, cations, DNA chains and organic compounds soluble in highly polar solvent like water.

BACKGROUND OF INVENTION

3-Hydroxyflavones (3-HF) are important fluorescent sensors due to their excited state intramolecular proton transfer (ESIPT) property originated from their normal (N*) and phototautomer forms (T*) (T. Ozturk, A. S. Klymchenko, A. Capan, S. Oncul, S. Cikrikci, S. Taskiran, B. Tasan, F. B. Kaynak, S. Ozbey, A. P. Demchenko, *Tetrahedron,* 2007, 63, 10290). This property provides 3-HF with well separated two emission bands on fluorescent spectroscopy, resulting from their excited normal and tautomeric forms, intensities of which are sensitive to their environment, including polarity and hydrogen bonding perturbations in the surrounding molecules (P. Chou, D. McMorrow, T. J. Aartsma, M. J. Kasha, *Phys. Chem.* 1984, 88, 4596). The changes in the peak intensities and in their corresponding ratios (N*/T*) have been well observed in proteins (A. Sytnik, D. Gormin, M. Kasha, *Proc. Natl. Acad. Sci. U.S.A.* 1994, 91, 11968), micelles (M. Sarkar, J. G. Ray, P. K. Sengupta, *Spectrochim. Acta Part, A* 1996, 52, 275) and polymers (J. R. Dharia, K. F. Johnson, J. B. Schlenoff, *Macromolecules* 1994, 27, 5167).

As the presence of electron donating groups at C-3 of 3-HFs improves their fluorescence strength, sensor researches related with 3-HFs have particularly been devoted to such materials. Ratiometric changes between the two peaks, depending on the corresponding changes at the surrounding environment of 3-HFs have created various applications, among which are sensing ions and moisture, recognition of organized systems like micelles and phospholipids (A. P. Demchenko, K.-C. Tang, P.-T. Chou, *Chem, Soc. Rev,* 2013, 42, 1379).

DISCLOSURE OF INVENTION

The invention discloses the compounds that are useful when employed as fluorescent sensors particularly to sense atoms and molecules having anion and cation properties, and organic and inorganic molecules having different polarities. They have potential of being used as sensors. The invention discloses the molecules having the formulas (I), (II) and (III).

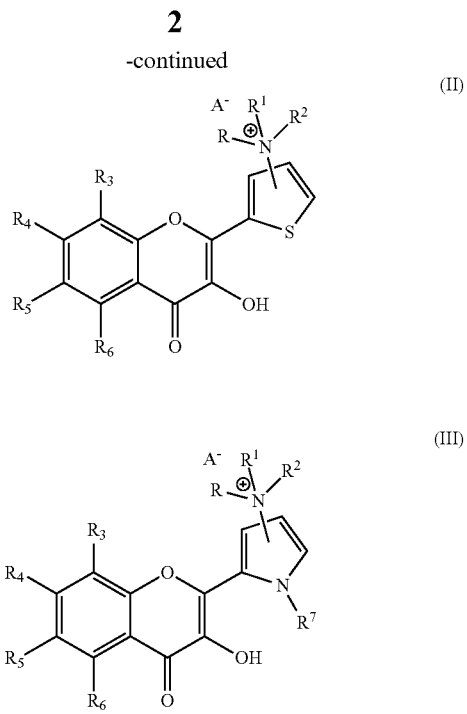

wherein $A = F^-, Cl^-, Br^-, I^-, CH_3OSO_3$ or $CH_3PhSO_3$, and $R, R^1, R^2, R^3, R^4, R^5, R^6$ and $R^7$ are independently or equally atom chain(s)/group(s) of about 1 atom to 60 atoms. They may equally or independently have one or more of a group comprising alkyl, aryl, alkenyl, alkynyl, amine, ester, carbonate ester, carbonyl, sulphide, organosilane and thiolate.

EXAMPLE

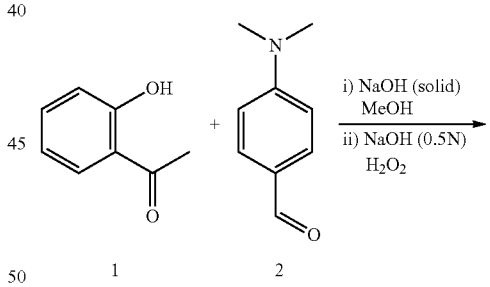

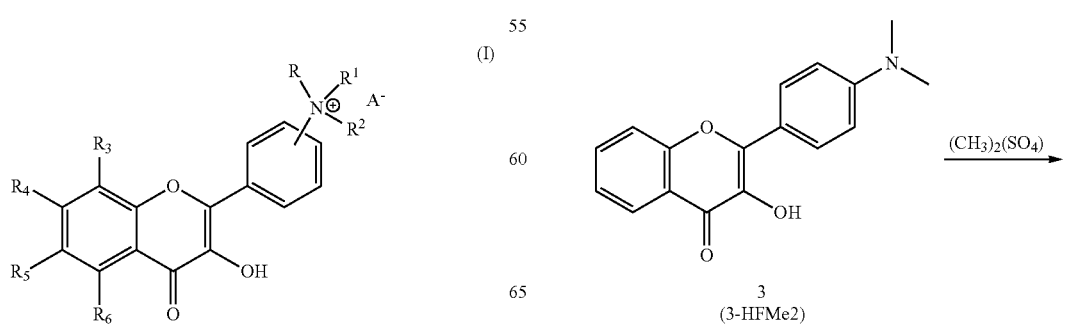

-continued

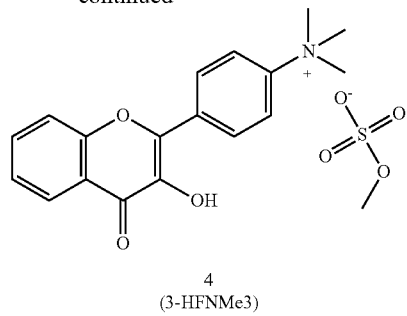

4
(3-HFNMe3)

A General Procedure for the Synthesis of 3-Hydroxyflavone Salt:

3-Hydroxyflavone (3-HF) 3 was synthesized following the literature procedure (S. Gunduz, A. C. Goren, T. Ozturk *Org. Lett.* 2012, 14, 1576). A solution of 3-HF 3 (0.37 g, 1.3 mmol) and dimethylsulfate (6.55 mmol, 0.62 ml) in THF was refluxed for 24 h. The precipitate was filtered after the mixture was reached room temperature. The crude solid was purified by Soxhlet extraction, using dichloromethane as solvent, which yielded N-(3-hidroksi-4'-flavonyl)-N,N,N-trimethylammonium sulphate (3-HFNMe3) 4 as a white solid (0.122 g, % 23). $^1$H NMR (600 MHz, $D_2O$) $\delta$ (ppm) 8.18 (d, 2H, J=8.4 Hz), 7.89 (d, 2H, J=7.6 Hz), 7.79 (d, 2H, J=8.4 Hz), 7.68 (t, 1H, J=7.6 Hz, J=7.5 Hz), 7.50 (d, 1H, J=7.6 Hz), 7.34 (t, 1H, J=7.6 Hz, J=7.5 Hz), 5.39 (s, 9H); $^{13}$C NMR (150 MHz, $D_2O$) $\delta$ (ppm) 157.2, 134.5, 132.1, 129.5, 129.4, 129.3, 125.1, 124.9, 124.4, 124.3, 119.8, 119.7, 118.3, 56.8, 53.8; MS (EI) m/z 405 $M^+ +1$ Fluorescence of 3-HFNMe3 4 in Water:

As 3-HFs are not soluble in water, a salt of 3-HF was prepared by methylation of dimethylamino moiety of 2-(4-(dimethylamino)phenyl)-3-hydroxy-4H-chromen-4-one (3-HFMe2) 3 to obtain N-(3-hydroxy-4'-flavonyl)-N,N,N-trimethylammonium sulphate (3-HFNMe3) 4 as a water soluble 3-HF. Although 3-HF is not soluble in water, emission of 3-HF in water was reported previously by Kahsa et al. (D. McMorrow, M. Kahsa *J. Phys. Chem.* 1984, 88, 2235). The possible explanation could be that 3-HF had a very low solubility in water, which was enough for their fluorescence measurements. As the amount of 3-HF dissolved in water is not know, such a measurement is not suitable for most of the measurements.

3-HFNMe3 is a highly water soluble salt. Its fluorescence in normal water gave only one emission band (excited at 381 nm) having a maximum of 456 nm (FIG. 1A). On the other hand, similar to the results obtained by Kasha et al. two bands appeared belonging to N* and T* bands at 450 and 520 nm, respectively (FIG. 1B). The only difference between two water samples is the presence of metal ions in normal water, which may interact with flavone resulting in a single emission. As ultra pure water does not have any trace of ion, two separate bands could be observed clearly.

DNA Chains Employed in Fluorescence Measurements

C25: A single-strain DNA chain, comprising 25 Cytosines

G25: A single-strain DNA chain, comprising 25 Guanines

A25: A single-strain DNA chain, comprising 25 Adenines

T25: A single-strain DNA chain, comprising 25 Thymines

C15-A5: A single-strain DNA chain, comprising 15 Cytosines and 5 Adenines

C10-A10: A single-strain DNA chain, comprising 10 Cytosines and 10 Adenines

C5-A15: A single-strain DNA chain, comprising 5 Cytosines and 15 Adenines

T15-G5: A single-strain DNA chain, comprising 15 Thymines and 5 Guanines

T10-G10: A single-strain DNA chain, comprising 10 Thymines and 10 Guanines

T5-G15: A single-strain DNA chain, comprising 5 Thymines and 15 Guanines

Fluorescence Measurements:

A stock solution of 3-hydroxyflavone sulphate salt (3-HFNMe3), dissolved in ultra pure water (2.1 mg, 2 ml, 2.5× $10^{-3}$ M), was prepared, from which 200 µl was transferred into a quartz cell (1×1×3 cm) and diluted to 2 ml with ultra pure water. Fluorescence emission was then recorded after each addition the DNA solution (2 µl, 20 nmol/ml). The ratio of N* and T* bands was calculated and a graph, having N*/T* ratio vs DNA concentration was plotted. Each experiment was repeated five times to understand the repeatability of the results, which gave the same results.

Gradual addition of DNA solution into the 3-HFNMe3 solution resulted in a ratiometric quenching of particularly the N* band, the ratio of which varied with the nature of DNA (FIG. 2-6). While N*/T* curve of C25 was calculated to be the highest, T25 had the lowest curve (FIG. 2). The curves of N*/T* ratios of A25 and G25, which took place between the highest and the lowest curves of C25 and T25, respectively, followed almost the same line. Each DNA experiment was repeated five times, which gave the same result. As it is known that 3-HFs are very sensitive to their environment, possible explanation could be that the DNA chains had varying interactions with 3-HFNMe3, due to their varying chemical structures and conformations, which affected the fluorescence intensities. The curves of the rest of the DNA chains C15-A5 (FIG. 3), C10-A10, C5-A15 (FIG. 4), T15-G5, T10-G10 and T5-G15 (FIGS. 5 and 6) took part between the DNA curves of C25 and A25.

As the experiments explained above prove that the flavone 3-HFNMe3 is an efficient sensor for identification of various chemical conformations, and a memory database could be created for various DNA chains.

Figure 1:
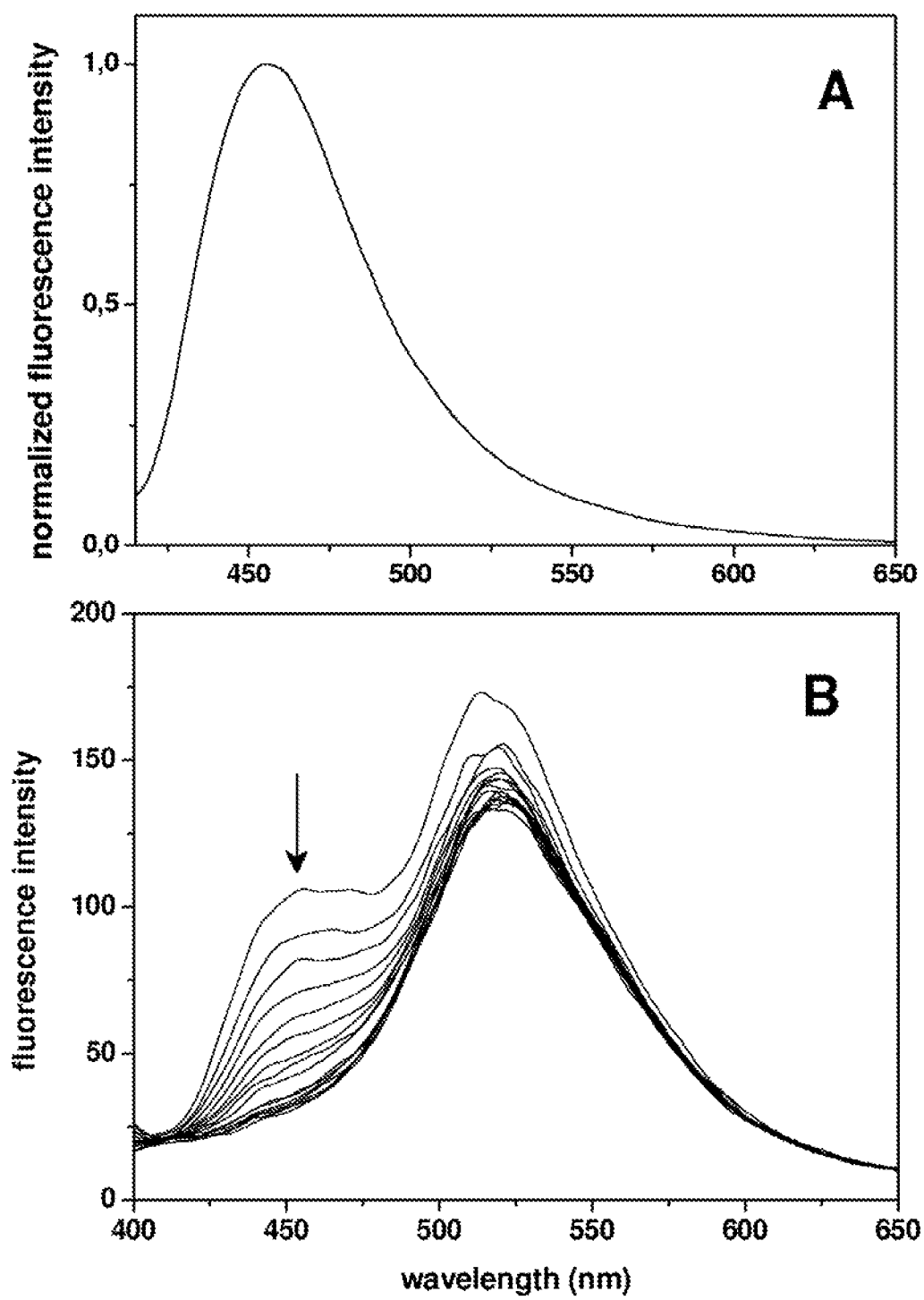
FIG. 1. Ratiometric decrease of N* band with the addition of DNA, excited at 381 nm. A) Tap water, B) Addition of DNA to the deionized water FIG. 2. N*/T* ratios of DNA solutions: C25, G25, A25 and T25
Figure 2:
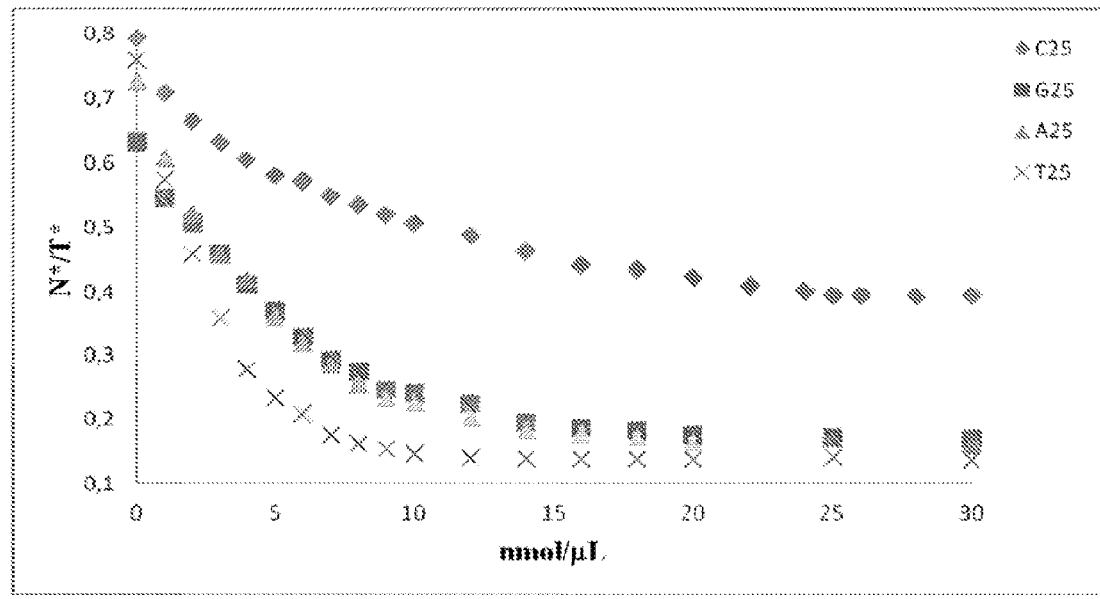
Figure 3:
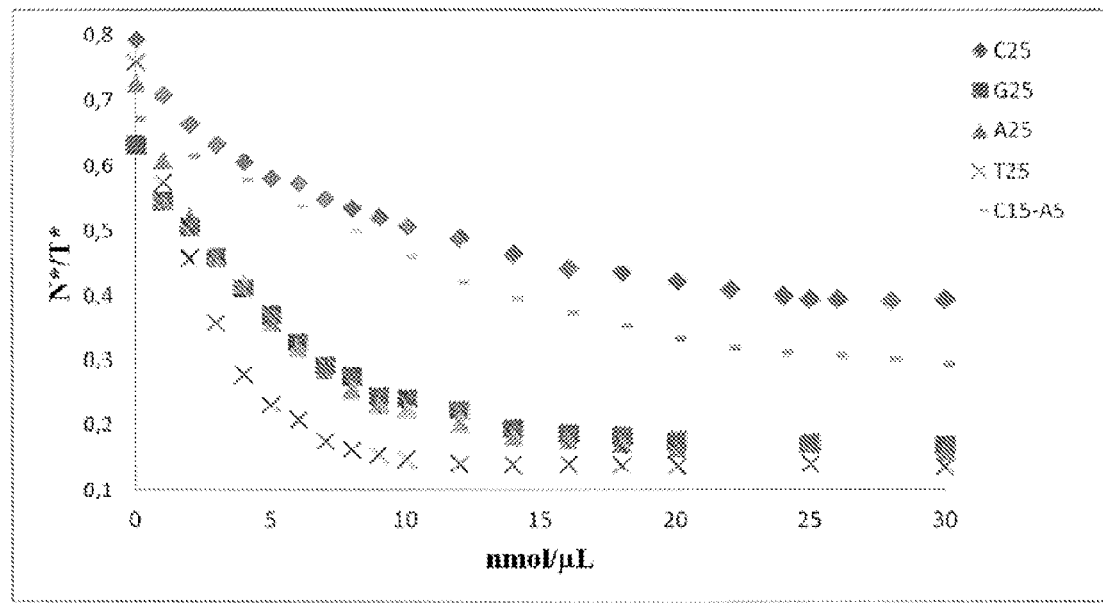
FIG. 3. N*/T* ratios of DNA solutions: C25, G25, A25, T25 and C15-A5
Figure 4:
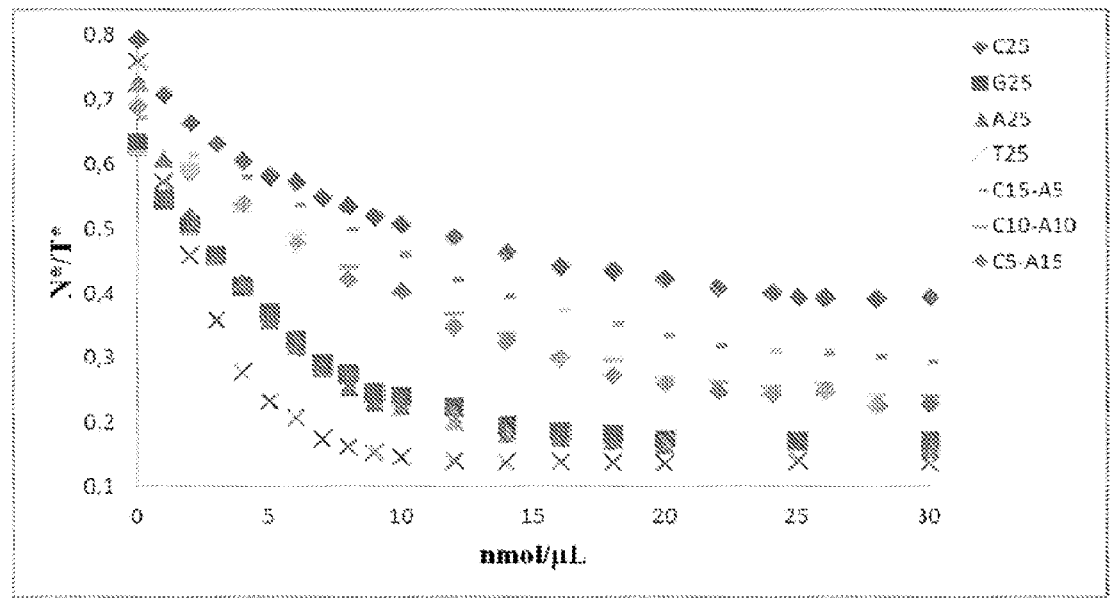
FIG. 4. N*/T* ratios of DNA solutions: C25, G25, A25, T25, C15-A5, C10-A10 and 05-A15
Figure 5:
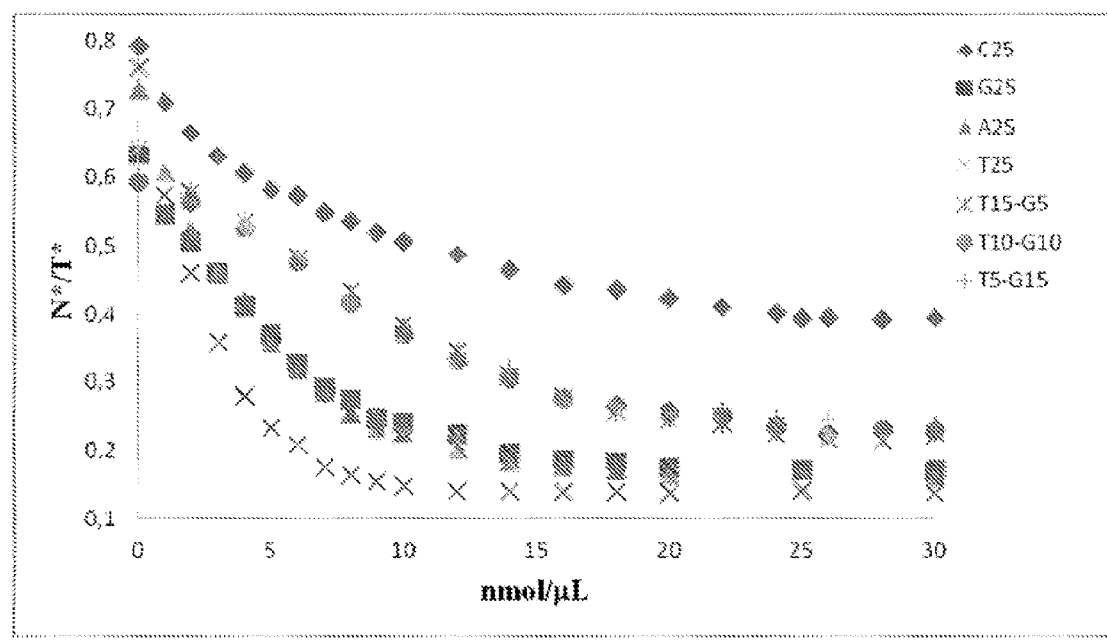
FIG. 5. N*/T* ratios of DNA solutions: C25, G25, A25, T25, T15-G5, T10-G10 and T5-G15
Figure 6:
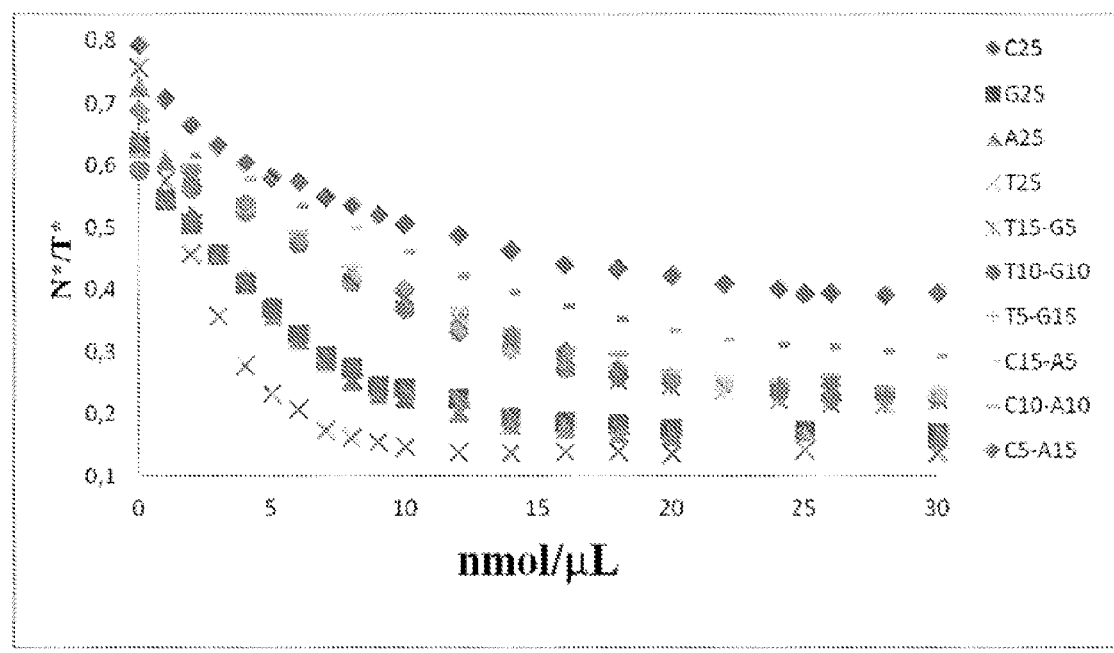
FIG. 6. N*/T* ratios of DNA solutions: C25, G25, A25, T25, C15-A5, C10-A10, C5-A15, T15-G5, T10-G10 and T5-G15

We claim:
1. Compound of formula (I)

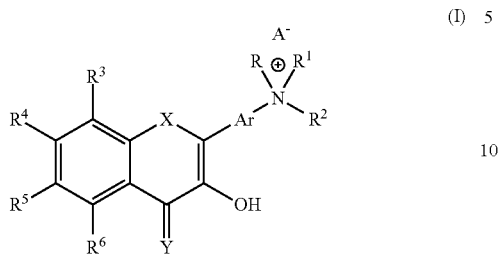

(I)

wherein
A=F, Cl, Br, I, $CH_3OSO_3$ or $CH_3PhSO_3$; R, $R^1$, $R^2$, $R^3$, $R^4$, $R^5$ and $R^6$ are independently or equally an atom or atom chain(s)/group(s) of about 1 atom to 60 atoms;
X=O, S or $NR^8$, in which R is an atom or atom chain(s)/group(s) of about 1 atom to 60 atoms;
Y=O or S; and Ar=aromatic group having 6 to 14 carbon atoms or aromatic heterocyclic group having 4, 5 or 6 carbon atoms and at least one heteroatom of N, S or O or aromatic fused heterobicycle having 6 to 9 carbon atoms and at least one heteroatom of N, S or O.

* * * * *